United States Patent [19]

Katsoyannis et al.

[11] Patent Number: 4,992,417
[45] Date of Patent: Feb. 12, 1991

[54] SUPERACTIVE HUMAN INSULIN ANALOGUES

[75] Inventors: Panayotis G. Katsoyannis, Manhasset; Gerald P. Schwartz, Washingtonville, both of N.Y.

[73] Assignee: Mount Sinai School of Medicine, New York, N.Y.

[21] Appl. No.: 273,967

[22] Filed: Nov. 18, 1988

Related U.S. Application Data

[63] Continuation-in-part of Ser. No. 74,558, Jul. 17, 1987 filed as PCT/US88/02289 on Jul. 7, 1988

[51] Int. Cl.$^5$ .................... C07K 7/40; A61K 37/02
[52] U.S. Cl. ........................ 514/3; 530/303; 514/866
[58] Field of Search ............ 530/303, 304; 514/3, 514/866

[56] References Cited

U.S. PATENT DOCUMENTS

| | | |
|---|---|---|
| 3,420,810 | 1/1969 | Katsoyannis et al. |
| 3,883,496 | 5/1975 | Geiger ............... 530/303 |
| 3,883,500 | 5/1975 | Geiger ............... 530/303 |
| 4,421,685 | 12/1983 | Chance et al. ...... 530/303 |
| 4,430,266 | 2/1984 | Frank ................. 530/303 |
| 4,459,228 | 7/1984 | Grime et al. ....... 530/303 |
| 4,569,791 | 2/1986 | Frank et al. ....... 530/303 |
| 4,569,792 | 2/1986 | Frank et al. ....... 530/303 |
| 4,581,165 | 8/1986 | Frank et al. |
| 4,652,547 | 3/1987 | Chance et al ...... 514/4 |
| 4,652,548 | 3/1987 | Chance et al. |

FOREIGN PATENT DOCUMENTS

0214826A2  3/1987  European Pat. Off.

OTHER PUBLICATIONS

Fischer, Biol. Chem. Hoppe-Seyler, 366, 521-525, May 1985.
Chemical Abstracts, vol. 101, 1984, p. 72, abstract No. 84120d.
Schwartz et al., "A Superactive Insulin: [B 10-Aspartic acid]Insulin (Human)", Proc. Nat'l Acad. Sci., U.S.A., vol. 84, pp. 6408-6411, Sep. 1987.
Chemical Abstracts, vol. 105, 1986, p. 87 abstract No. 184142p.
Chemical Abstracts, vol. 97, 1982, p. 909, abstract No. 216734t.
Botstein, D. and Shortle, D., Strategies and Applications of in Vitro Mutagenesis, Science, vol. 229, pp. 1193-1201, 1985.
Brange et al., "Monomeric Insulins Obtained by Protein Engineering and Their Medical Implications", Nature, 33:679 (Jun. 16, 1988).
Chance, R. E., Hoffman, J. A., Kroeff, F. P., Johnson, M. G., Schirmer, E. W., and Bromer, W. W., The Lilly Research Labs., Ind.
Katsoyannis, P. G., Tometsko, A. and Zalut, C., Insulin Peptides, XII, Human Insulin Generation by Combination of Synthetic A & B. Chains, Journal of the American Chemical Society, 88, 166, 1966.
Schwartz C. P., Burke, C. T. and Katsoyannis, P. G., [12-Asparagine-B] Human Insulin—An Analogue With Modification in the Hydrophobic Core of Insulin, Int. J. Peptide Protein Res. 17, pp. 243-255, 1981.
Katsoyannis, P. G. and Tometsko, A., Insulin Synthesis By Recombination of A and B Chains: A Highly Efficient Method, Proceedings of the Natl. Acad. of Sciences, vol. 55, No. 6, pp. 1554-1561, 1966.
Schwartz, G. P. and Katsoyannis, P. G., Insulin Peptides, Part XXIII. The Syntheses of a Hexadecapeptide Derivative Related to the B Chain of Human Insulin, Journal of the Chemical Society, Perkins Transactions I, 1973.
Schwartz, G. P. and Katsoyannis, P. G., Insulin Peptides. Part XXIV. A Novel Synthesis of the Human Insulin B Chain S-Sulphonate, Journal of the Chemical Society, Perkin Transactions I, 1973.

(List continued on next page.)

Primary Examiner—F. T. Moezie
Attorney, Agent, or Firm—Brumbaugh, Graves, Donohue & Raymond

[57] ABSTRACT

Superactive insulin analogues are provided. These insulin analogues are used in therapeutically effective amounts in the preparation of pharmaceutical compositions for administration to diabetic patients.

9 Claims, 5 Drawing Sheets

OTHER PUBLICATIONS

Chan, S. J., Seino, S., Gruppuso, P. A., Schwartz, R., Steiner, D. F., A Mutation in the B Chain Coding Region is Associated With Impaired Proinsulin Conversion in a Family With Hyperproinsulinemia, Proc. Natl. Acad. Sci. U.S.A., vol. 84, pp. 2194–2197, 1987.

Katsoyannis, P. G., Tometsko, A, Zalut, C., Johnson, S. and Trakatellis, A. C., Studies on the Synthesis of Insulin From Natural and Synthetic A and B Chains. I. Splitting of Insulin and Isolation of the S–Sulfonated Derivatives of the A and B Chains, Biochemistry, v, pp. 2635–2642, 1967.

Katsoyannis, P. G., Trakatellis, A. C., Johnson, S., Zalut, C. and Schwartz, G., Studies on the Synthesis of Insulin from Natural and Synthetic A and B Chains, II. Isolation of Insulin from Recombination Mixtures of Natural A and B Chains, Biochemistry, 6, pp. 2642–2655, 1967.

Katsoyannis, P. G., Trakatellis, A. C., Zalut, C., Johnson, S. Tometski, A., Schwartz, G., and Ginos, J., Studies on the Synthesis of Insulin from Natural and Synthetic A and B Chains. III. Synthetic Insulins, Biochemistry, pp. 2656–2668, 1967.

Schwartz, G. and Katsoyannis, P. G., Synthesis of Human [9-Leucine-B]Insulin, Biochemistry, 15, pp. 4071–4076, 1976.

Schwartz et al., J. Chem. Research (M), The Synthesis of [10-Leucine-B ] Human Insulin, A Biologically Active Analogue, pp. 2453–2466, 1977.

Schwartz, G. P. and Katsoyannis, P. G., The Synthesis of [10-Leuicine-B] Human Insulin, a Biologically Active Analogue, Journal of Chem. Res. (S), pp. 220–221, 1977.

Katsoyannis, P. G., Structure and Function Relationships In Insulin: A Synthetic Approach, Elsvier North Holland, Inc., pp. 171–192, 1980.

Katsoyannis, P. G., New Synthetic Insulins, Treatment of Early Diabetes, pp. 319–328, 1979.

Burke, G. T., Schwartz, G. and Katsoyannis, P. G., Nature of the $B^{10}$ Amino Acid Residue, Int. J. Peptide Protein Res., 23, pp. 384–401, 1984.

Schwartz, G., Burke, G. T., and Katsoyannis, P. G., The Importance Of the $B^{10}$ Amino Acid Residue to the Biological Activity Of Insulin. [$Lys^{10}$–B] Human Insulin, Journal of Protein Chemistry, vol. 1, No. 3, pp. 177–189, 1982.

Ferderigos, N., Cosmatos, A., Ferderigos, A. and Katsoyannis, P. G. [21-Arginine-A] Insulin–A Biologically Active Analog, Int. J. Peptide Protein Res. 13, pp. 43–53, 1979.

Cosmatos, A., Ferderigos, N., and Katsoyannis, P. G., Chemical Synthesis of [Des(Tetrapeptide $B^{27-30}$), TYR($NH_2$)$^{26}$-B] and [DES (Pentapeptide $B^{26-30}$), PHE($NH_2$)$^{25}$-B] Bovine Insulins, Int. J. Peptide Protein Res. 14, pp. 457–471, 1979.

Schwartz, G. and Katsoyannis, P. G., Synthesis of Des(tetrapeptide $B^{1-4}$) and Des(pentapeptide $B^{1-5}$) Human Insulins. Two Biologically Active Analogues, Biochemistry, 17, pp. 4550–4556, 1978.

The Effect of Modifications of the $A^5$ and $A^{19}$ Amino Acid Residues on the Biological Acitivity of Insulin. [$Leu^5$-A] and [$Phe^{19}$-A] Sheep Insulins, Journal of Protein Chemistry, vol. 2, pp. 147–170, 1983.

Schwartz, G., Burke, G. T., Chanley, J. D., and Katsoyannis, P. G., An Insulin Analogue Possessing Higher in Vitro Biological Activity Than Receptor Binding Affinity. [21-Proline-B]Insulin, Biochemstry] vol. 22, pp. 4561–4567, 1983.

Kitagawa, K., Ogawa, H., Burke, G. T., Chanley, J. D., and Katsoyannis, P. G., Critical Role of the $A^2$ Amino Acid Residue in the Biological Activity of Insulin: [2––Glycin-A]-and [2-Alanine-A]Insulins, Biochemistry, vol. 23, pp. 1405–1413, 1984.

Kitagawa, K., Ogawa, H., Burke, G. T., Chanley, J. D., and Katsoyannis, P. G., Interaction between the $A^2$ and $A^{19}$ Amino Acid Residues Is of Critical Importance for High Biological Activity in Insulin: [19-Leucine-A]Insulin, Biochemistry, vol. 23, pp. 4444–4448, 1984.

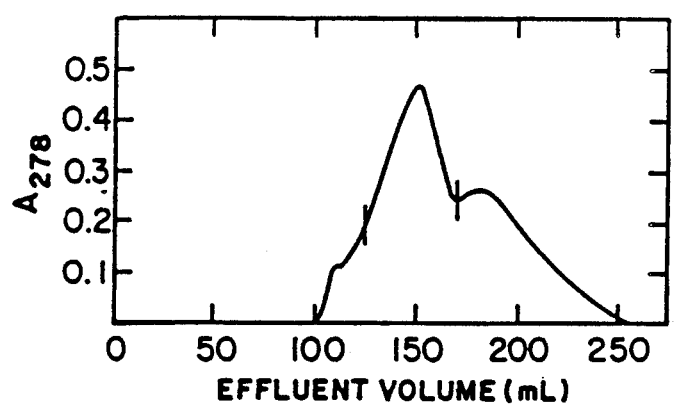
FIG. 1
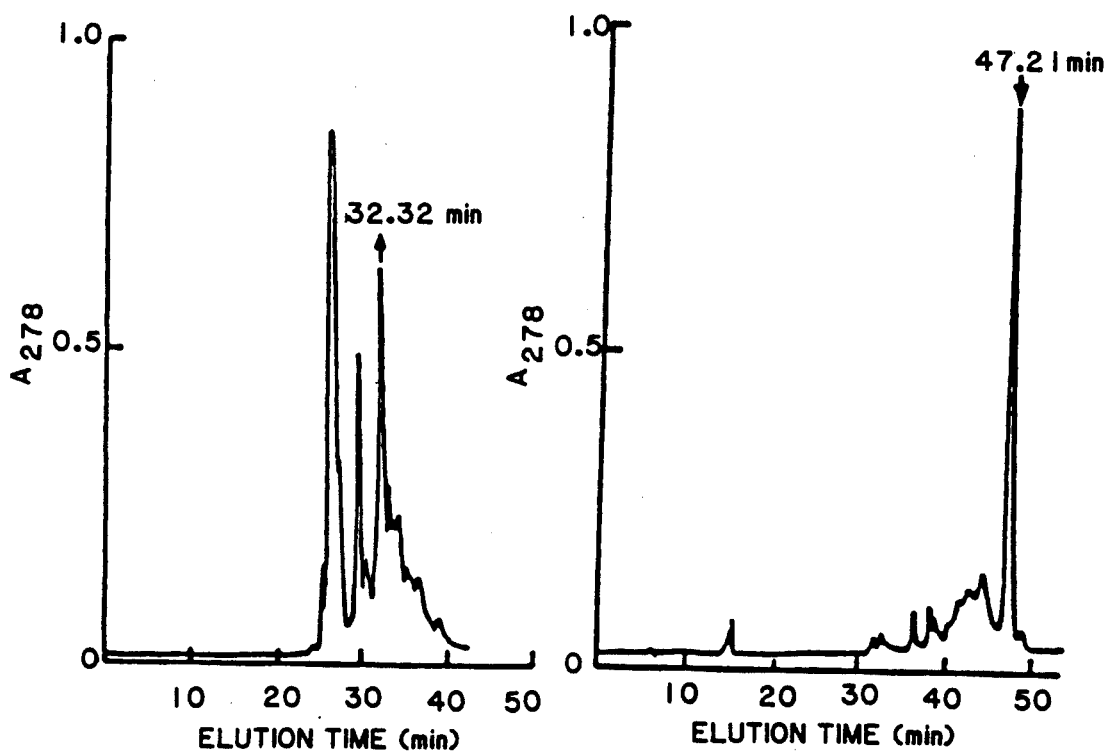
FIG. 2a
FIG. 2b

SUPERACTIVE HUMAN INSULIN ANALOGUES

This application is a continuation-in-part of U.S. application Ser. No. 074,558, filed July 17, 1987.

BACKGROUND OF THE INVENTION

The present invention relates to novel superactive insulin analogues and their use in pharmaceutical compositions for the treatment of diabetes.

Insulin is a hormone which has a key role in the regulation of growth and metabolism in vertebrates. Severe metabolic derangements occur in the absence of insulin resulting from the failure of many cells to utilize glucose and amino acids normally. The inability to metabolize glucose leads in man to diabetes mellitus, a complex chronic metabolic disorder in which there is abnormal carbohydrate, fat and protein metabolism. In its most fully expressed clinical form, diabetes mellitus is characterized by an absolute or relative deficiency of insulin or insulin activity and is associated with glucosuria, ketonuria, growth arrest, and negative nitrogen balance. These conditions can ultimately lead to death from acute metabolic acidosis caused by unrestrained oxidation of fatty acids or inanition which results from the lack of sufficient lipid reserves needed to generate ketone bodies. Inanition is defined as a condition characterized by marked weakness, extreme weight loss, and a decrease in metabolism resulting from prolonged and severe insufficiency of food. *Dorland's Illustrated Medical Dictionary*, 25th Edition.

The discovery and purification of insulin in the 1920's and its association with diabetes mellitus provided the means to intervene in the disease. See, e.g., Bliss, *The Discovery of Insulin* (1983), University of Chicago Press, Chicago, Ill. Today, insulin administration to diabetic patients is the primary therapeutic means for controlling the disease.

Insulin is a 6000 dalton polypeptide which is composed of two short peptide chains, termed A and B, which are linked to each other by invariant disulfide bridges. In almost all insulins studied, the A chain, which is 21 amino acids long, also contains an internal disulfide bridge. The B chain is 30 amino acids in length. Like many eukaryotic proteins, insulin is synthesized in a precursor form which is post-synthetically processed to the mature two polypeptide chain active hormone.

The immediate precursor of insulin is proinsulin, a single chain polypeptide composed of the B and A chains linked to a connecting peptide of approximately 31 amino acids, termed the C-peptide, by adjacent pairs of basic residues. The order of the three peptides in the proinsulin molecule is $NH_2$-B chain-Arg-Arg-C-peptide-Lys-Arg-A chain-COOH. The translation product of insulin mRNA, however, is preproinsulin which is proinsulin that contains at its $NH_2$ terminus a 24 amino acid largely hydrophobic signal peptide characteristic of proteins that are either transported through or inserted into cellular membranes.

Preproinsulin is synthesized in pancreatic beta cells located within the islets of Langerhans which are dispersed throughout the pancreas. Removal of the signal peptide occurs in the rough endoplasmic reticulum with the resulting fully folded oxidized proinsulin being transported to the Golgi apparatus for packaging into secretion granules. The folded proinsulin is stabilized by disulfide bonds. During maturation of the secretion granules, the folded proinsulin molecule is cleaved by specific proteases at the paired basic residues to liberate insulin and the C-peptide.

As discussed above, therapy for diabetes mellitus includes administration of controlled amounts of insulin to the diabetic patient. The insulin so administrated has, for the most part, been obtained from animal pancreases, notably bovine and porcine. Bovine and porcine insulins function to maintain hormonal homeostasis in the same way as human insulin with about the same potency but, because they are foreign proteins, can elicit an immunological response which diminishes their usefulness. More recently, human insulin, generated by recombinant DNA techniques, has been added to the therapeutic armamentarium. The use of human insulin, produced by recombinant DNA or other techniques, is not likely to produce the adverse immunological problems attendant the use of animal insulins. Even with the availability of natural human insulin, however, administration of the hormone to diabetics has not been always sufficient to restore normal metabolism. There is thus a need for alternative insulins with better activity or other means of therapy for diabetes.

Familial hyperproinsulinemia is a genetic disorder characterized by a marked increase in serum proinsulin-like molecules. Three families with this rare disorder have been identified. In two of the families a structurally abnormal proinsulin-like molecule was seen. The genetic defect was identified as a mutation causing an amino acid substitution in proinsulin which results in incomplete cleavage of proinsulin by the proteases which form insulin.

The affected members of the third family produced a proinsulin-like molecule of about the same size as proinsulin that behaved like the normal prohormone in receptor binding assays. Sequence analysis of cloned insulin genes obtained from two affected members from this third family revealed a single coding mutation which substituted an aspartic acid for histidine in the proinsulin molecule at a position which corresponds to position 10 of the B chain of insulin. Chan et al., Proc. Natl. Acad. Sci. (1987), vol. 84, pp. 2194–2197. The mutation was believed to inhibit further processing of proinsulin to insulin, thus resulting in the accumulation of the mutant proinsulin. The precise way the mutation inhibits further processing is not currently known. A human insulin analogue, [10-Aspartic acid-B] human insulin, which corresponds to this mutant proinsulin, has now been synthesized and has been shown to have greater potency than natural insulins.

It has also been found that the elements of the carboxyl terminal of the B chain of insulin appear also to influence the biological activity of insulin. Specifically, the B25 site appears also to play a role in the potency of insulin analogues.

Elimination of the C-terminal pentapeptide sequence of the B-chain of insulin, and amidation of the carboxyl group of the newly-formed C-terminus, Phe B25, results in an analogue, des-pentapeptide(B26-B30)-[Phe$^{B25}$-α-carboxamide]insulin, which has been shown to display comparable potency with the natural hormone. See Nakagawa et al., *J. Biol. Chem.*, 261:7332–41(1986); Cosmatos et al., *Int. J. Pept. Prot. Res.*, 14:457–71 (1979); Casareto et al., *Biol. Chem. Hoppe-Seyler*, 368:709–16 (1987). Substitution of Phe B25 with several other amino acid residues, as well as various modifications of the B26-B30 segment of these substituted insulins, led to analogues varying in potency from almost total inactivity to potency higher than natural insulin. Nakagawa et al., J. Biol. Chem., 261, supra; Casareto et al., supra; Nakagawa et al., J. Biol. Chem., 262:10254–58 (1987). Among these, des-pentapeptide(B26-B30)-[Tyr$^{B25}$-α-carboxamide]insulin and its His$^{B25}$ analogue display potency about 270–300% greater than insulin. Based upon these studies, it has been suggested that the B25 amino acid residue of insulin interacts with the receptor, thereby initiating conformational changes in as yet undefined areas of the insulin molecule which are involved in hormone-receptor binding. The B25-receptor interaction may be modulated in a positive or negative manner by the C-terminal B-chain domain, depending on the nature of the modifications to the B25 residue and the extent to which the B chain C-terminal domain has been altered. Nakagawa et al., J. Biol. Chem., 261, supra; Casareto, supra; Nakagawa et al., J. Biol. Chem., 262, supra.

Another human insulin analogue, des-pentapeptide (B26-B30)-[Asp$^{B10}$, Tyr$^{B25}$-α-carboxamide] insulin has also been synthesized and shown to have greater potency than natural insulins.

SUMMARY OF THE INVENTION

In accordance with the present invention, a superactive insulin analogue, [10-Aspartic acid-B] human insulin having the formula

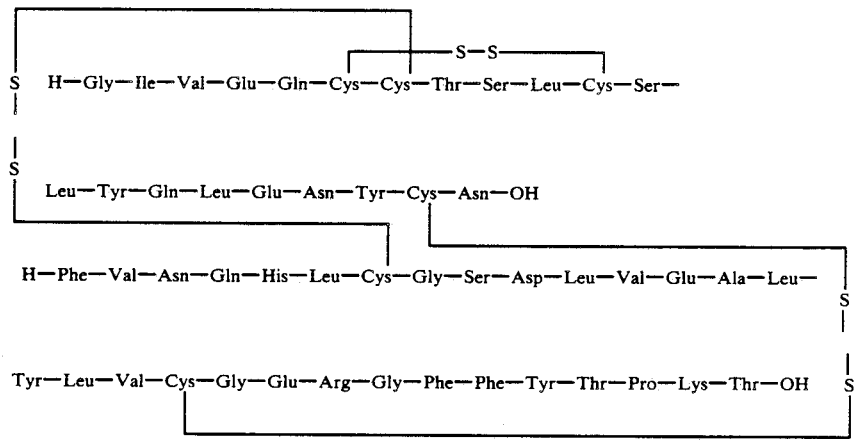

is provided. This insulin analogue (herein "10-Aspartic acid-B") demonstrates significantly greater potency than natural human insulin which has histidine at position 10 of the B chain.

Also in accordance with the present invention, a superactive insulin analogue, des-pentapeptide (B26-B30)-[Asp$^{B10}$, Tyr$^{B25}$-α-carboxamide] human insulin (herein "Asp$^{B10}$ analogue"), having the formula.

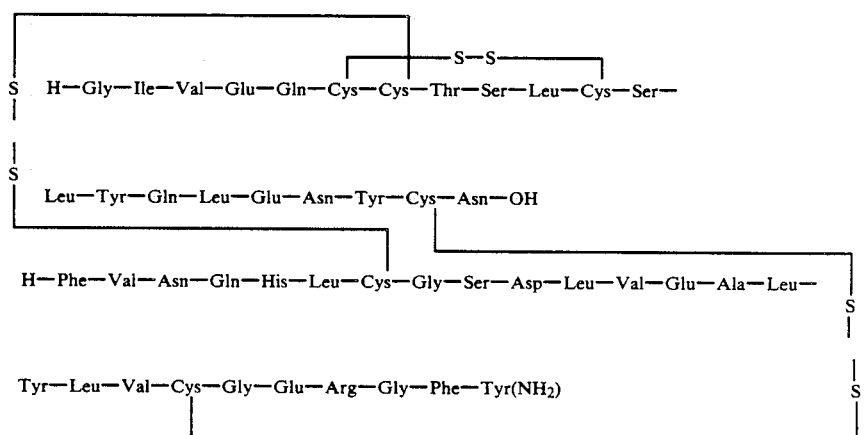

is provided. In addition to changes at the 10 position of the B chain the B26-B30 segment has been eliminated and Phe B25 has been substituted with Tyr-α-carboxamide. This insulin analogue demonstrates even greater potency than the [10-Aspartic acid-B] human insulin.

Another analogue, des-pentapeptide (B26-B30)-[Glu$^{B10}$, Tyr$^{B25}$-α-carboxamide] human insulin (herein "Glu$^{B10}$ analogue"), which differs from the previous analogue in that instead of Asp at position B10, it contains Glu having the formula:

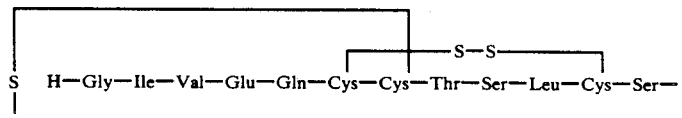

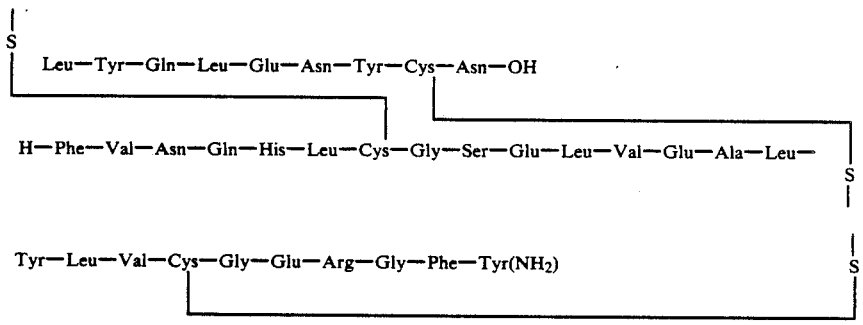

This insulin analogue is at least 20X more active than natural insulin.

It is believed that further substitution of the B10 amino acid residue (x) in the molecule des-pentapeptide (B26-B30)-[X$^{B10}$, Tyr$^{B25}$-α-carboxamide] insulin (where X is the residue to be substituted) with α-aminoadipic acid or higher homologues or even with other unnatural acidic amino acids, will lead to insulin analogues with even greater potency. It is also believed that the hydrophobic character of the backbone of acidic amino acid substituted at the B10 position is a contributing factor to the higher potency displayed by these analogues. Consequently substitution of the B10 amino acid residue (x) with a variety of amino acids having a hydrophobic backbone, in a ring structure or in an open chain, bearing also a free carboxyl or other charged moiety, may also lead to other highly potent insulin analogues.

The invention also relates to pharmaceutical compositions for the treatment of diabetes in patients needing such treatment which comprise a therapeutically effective amount of a human insulin analogue selected from the group consisting of [10-Aspartic acid-B] human insulin, des-pentapeptide (B26-B30)-[Asp$^{B10}$, Tyr$^{B25}$-α-carboxamide] human insulin, des-pentapeptide (B26-B30)- [Glu$^{B10}$, Tyr$^{B25}$-α-carboxamide] or higher B10 homologues together with a pharmaceutically acceptable carrier.

Furthermore, the invention relates to a method for treating diabetes comprising administering to a diabetic patient in need of insulin therapy a therapeutically effective amount of a human insulin analogue selected from the group consisting of [10-Aspartic acid-B] human insulin, des-pentapeptide (B26-B30)-[Asp$^{B10}$, Tyr$^{B25}$-α-carboxamide] human insulin, or any of the other abovementioned B10 analogues together with a pharmaceutically acceptable carrier.

BRIEF DESCRIPTION OF THE DRAWINGS

FIG. 1 is a chromatogram showing the elution of crude human [10-Aspartic acid] B chain S-sulfonate from a CM-cellulose column.

FIG. 2 is an HPLC chromatogram showing the elution of the combination mixture of human A chain S-sulfonate and human [10-Aspartic acid] B chain S-sulfonate. Panel A shows the initial chromatographic separation. Panel B depicts the rechromatography of the material in the peak eluting at 32.32 min shown in Panel A.

DESCRIPTION OF THE INVENTION

Figure 4:
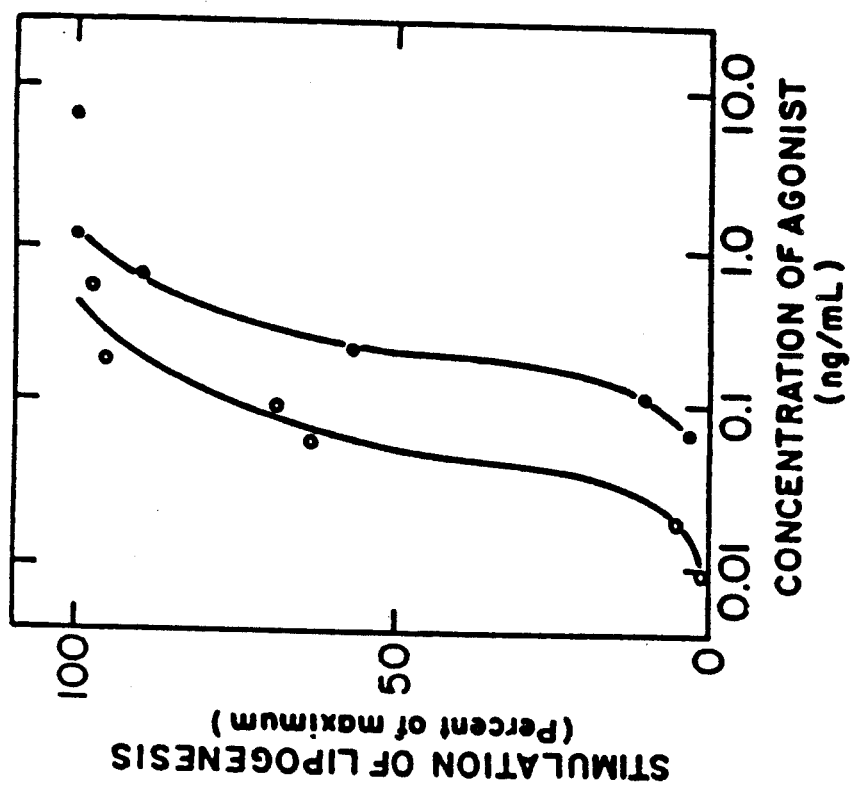
FIG. 4 is a graph showing the effect of [10-Aspartic acid-B] human insulin and bovine insulin on the stimulation of lipogenesis in rat adipocytes.

The present invention provides a superactive insulin analogue [10-Aspartic acid-B] human insulin of the formula

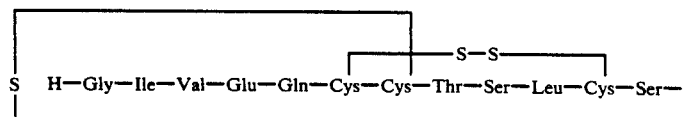

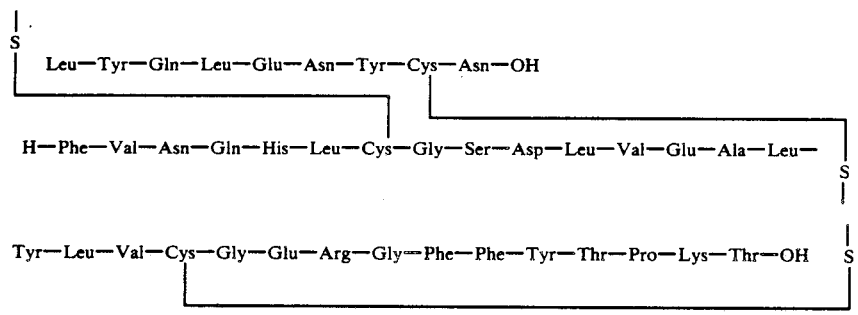

The present invention also relates to a superactive insulin analogue, des-pentapeptide (B26-B30)-[Asp$^{B10}$, Tyr$^{B25}$-α-carboxamide] human insulin of the formula

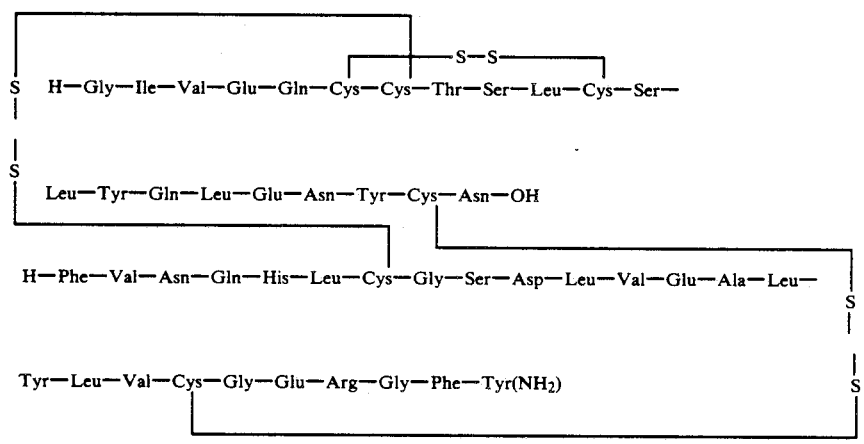

and the Glu$^{B10}$, α-amino-adipic acid$^{B10}$ or higher B10 homologues.

The term insulin analogue refers to a protein which has the basic A chain and B chain structure of human (and other species of) insulin and contains all of the half cysteine residues in the same position as present in native insulin. Thus, insulin analogues retain the disulfide bridge arrangement of natural insulins. Useful insulin analogues can differ from native insulins by the addition, deletion, substitution or modification of one or more amino acids in one or both chains of the molecule, but must retain at least some portion of insulin potency. See e.g. Katsoyannis, *Treatment of Early Diabetes* (1979), pp. 319–327, Plenum Publ. Corp.; Blondell, Adv. Prot. Chem. (1972), vol. 26, pp. 330–362.

The insulin analogues of the invention which differ from human insulin by the substitution of aspartic acid or glutamic acid for histidine at position 10 of the B chain and/or the elimination of the B26-B30 segment with substitution of PheB25 with Tyr-α-carboxamide, were unexpectedly found to have greater potency than natural insulins, especially those used in diabetes therapy.

[10-Aspartic acid-B] human insulin, des-pentapeptide (B26-B30)-[Asp$^{B10}$, Tyr$^{B25}$-α-carboxamide] human insulin or other B10-substitued analogues can be produced by any of a variety of techniques known to those skilled in the art. For example, the component A and B chains of the insulin analogue can be synthesized by any of the known peptide synthesis techniques, including solid phase peptide synthesis techniques and solution techniques, e.g. fragment condensation. See, e.g. Erickson and Merrifield, *The Proteins* (1976), vol. 2, chapter 3, Academic Press, New York; Blake et al. Proc. Natl. Acad. Sci. (1983), vol. 80, pp. 1556–1559 for a discussion of peptide synthesis techniques. The human insulin analogues can also be prepared by combining human or porcine A chains, isolated following reduction or oxidative sulfitolysis of intact pancreatic or recombinant insulin, with a [10-Aspartic acid], a des-pentapeptide (B26-B30)-[Asp10, Tyr-α-carboxamide25] or Glu$^{B10}$ B chain or analogues thereof prepared by peptide synthetic techniques or recombinant DNA methods. It is known that the A chains of porcine and human insulins are identical to each other in amino acid sequence, so that porcine A chain can readily substitute for human A chains in any method of producing [10-Aspartic acid-B] human insulin, des-pentapeptide (B26-B30)-[Asp$^{B10}$, Tyr$^{B25}$-α-carboxamide] or Glu$^{B10}$, human insulin analogues. Other A chain analogues could also be combined with the altered B chains of this invention.

Recombinant DNA methods for producing the human insulin B chain having aspartic acid, glutamic acid, or α amino-adipic acid or higher homologues at position 10 and/or elimination of the B26-B30 segment and substitution of Tyr-α-carboxamide for Phe at position 25 include, but are not limited to, cloning and expression of an in vitro synthesized DNA which codes for such a B chain amino acid sequence. Alternatively, an organism, such as bacteria, which expresses human insulin B chain could be induced to produce a modified B chain by any of the techniques of in vitro site-directed mutagenesis. See e.g. Smith, Ann. Rev. Genet. (1985), vol. 19, pp. 423–463; Botstein et al. Science (1985), vol. 229, pp. 1193–1201.

In general, to prepare [10-Aspartic acid-B] human insulin, des-pentapeptide (B26-B30)-[Asp$^{B10}$, Tyr$^{B25}$-α-carboxamide] human insulin, or other B10 modified analogues human or porcine insulin A chains, obtained by any known technique are combined with modified human B chains prepared by any convenient technique. The A and modified B chains are preferably in their stabilized S-sulfonated forms which can then be recombined by known procedures to form the intact active human insulin analogue. Known recombination techniques are taught by U.S. Pat. Nos. 3,420,810 to Katsoyannis and 4,421,685 to Chance et al. For example, U.S. Pat. No. 4,421,685 provides a single step process for forming an insulin which involves bringing together an S-sulfonated A chain and S-sulfonated B chain in the presence of a thiol reducing agent, such as dithiothreitol or cysteine, in an aqueous medium. The conditions for recombination include (1) a pH of about 8 to 12, (2) a total protein concentration of about 0.1 to 50 mg/ml, and (3) a thiol reducing agent in a concentration which produces about 0.4 to 2.5 SH groups per each —S—SO$_3$ group present in the total A and B chain S-sulfonates present in the mixture. The formation of [10-Aspartic acid-B] human insulin, des-pentapeptide (B26-B30)-[Asp$^{B10}$, Tyr$^{B25}$-α-carboxamide] human insulin, or any of the other B$^{10}$ substituted analogues occur by maintaining the reaction at a temperature of about 0° to 25° C. in an environment which provides a source of oxygen to allow the formation of the insulin S—S bonds.

Once the recombination reaction has been completed, the insulin analogue can be isolated and assayed for purity and activity by a variety of techniques known to those skilled in the art. Commonly employed techniques for purification of insulin and insulin analogues are chromatographic techniques, such as high performance liquid chromatography (HPLC), gel filtration and ion-exchange chromatography. Purity of the product can be determined by a variety of techniques including inter alia HPLC, polyacrylamide gel electrophoresis, amino acid analysis and amino acid sequencing.

Although insulin analogues, in general, maintain some residual insulin activity, the potency of such analogues is usually only a fraction of that of natural insulins. The potency of human, bovine and porcine insulins in U.S. Patent standards is about 25–26 IU (international units) per mg protein. Surprisingly [10-Aspartic acid-B] human insulin was determined to be about 4-6 times more potent than natural insulins in assays which measure the potency of insulin, des-pentapeptide (B26-B30)-[Asp$^{B10}$, Tyr$^{B25}$-α-carboxamide] human insulin was found to be approximately 11-13 times more potent than natural insulin and the Glu$^{B10}$ analogue was 20 times more potent than natural insulin.

Standard assays for measuring insulin potency include inter alia (1) insulin radioreceptorassays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction; (2) lipogenesis assays, performed e.g. with rat adipocytes, in which relative insulin potency is defined as the ratio of insulin to insulin analogue required to achieve 50% of the maximum conversion of [3-$^3$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radioimmunoassays which can determine the immunogenicity of insulin analogues by measuring the effectiveness by which insulin or an insulin analogue competes with $^{125}$I-insulin in binding to specific anti-insulin antibodies; and (5) other assays which measure the binding of insulin or an insulin analogue to cells, such as cultured lymphocytes, known to possess specific insulin receptors. In standard assays to measure relative insulin potency, e.g. assays (1), (2) and (5) listed above, [10-Aspartic acid-B] human insulin was determined to be about 4-6 times more active than natural insulins, des-pentapeptide (B26-B30)-[Asp$^{B10}$, Tyr$^{B25}$-α-carboxamide] human insulin was found to be 11-13 times more potent than natural insulins and the Glu$^{B10}$ analogue was 20 times more potent than natural insulin.

The human insulin analogues of the invention may also be formulated into pharmaceutical compositions for administration to diabetic patients. The pharmaceutical compositions comprise a human insulin analogue selected from the group consisting of [10-Aspartic acid-B] human insulin, des-pentapeptide (B26-B30)-[Asp$^{B10}$, Tyr$^{B25}$-α-carboxamide] human insulin or any other B10 analogues in an amount which is therapeutically effective in promoting the attainment of hormonal homeostasis in the diabetic patient together with a pharmaceutically acceptable carrier. As with all insulin preparations for treatment of diabetes, adequate therapeutic amounts of the active compound to achieve hormonal homeostasis in individual patients must be determined. Factors to be considered include the severity of the diabetic condition and the route of administration of the composition. Ultimately the particular physician treating the diabetic patient has discretion in the amount of the pharmaceutical composition and route of administration. Natural insulins are generally given to a patient in a therapeutic dosage to afford about 0.02 to about 5 units of human insulin activity per kilogram body weight per day. See e.g. U.S. Pat. No. 4,652,547.

Because these novel insulin analogues are more potent than natural insulin in vitro, it is believed that therapeutic amounts of them required to achieve homeostasis in diabetic patients may be less than the therapeutic amount of natural insulins now used to treat diabetes. In addition, another important advantage of these insulin analogues is faster clearance from the blood of diabetic patents. It is known that insulin clearance from the blood is mediated by the insulin receptor on cells. Since [10-Aspartic acid-B] human insulin had been shown to bind to the insulin receptor about five times more tightly, des-pentapeptide (B26-B30)-[Asp$^{B10}$, Tyr$^{B25}$-α-carboxamide] human insulin eleven to thirteen times and the Glu$^{B10}$ analogue 20 times more tightly than natural insulins, it is believed that these insulin analogues will be cleared from the blood of patients at a faster rate than natural insulins. As a consequence, it is believed in treatment for diabetics that vascular toxicity associated with the growth-promoting effects of circulating insulin may be lessened by the use of [10-Aspartic acid-B] human insulin, des-pentapeptide (B26-B30)-[Asp$^{B10}$, Tyr$^{B25}$-α-carboxamide] human insulin, the Glu$^{B10}$ analogue, or other αamino-adipic acid or higher B10 homologues.

Pharmaceutical compositions containing a therapeutically effective amount of an insulin analogue selected from the group consisting of [10-Aspartic acid-B)] human insulin, des-pentapeptide (B26-B30)-[Asp$^{B10}$, Tyr$^{B25}$-α-carboxamide] human insulin, the Glu$^{B10}$ analogue or other α amino-adipic acid or higher B10 analogues may be administered parenterally to a diabetic patient in need of insulin treatment. Preferably the composition is administered intramuscularly, subcutaneously or intravenously. The composition may also be administered to the patient by nasal spray. Alternatively, for long-term controlled homestasis, the composition may be incorporated into an implantable pump for administration to the patient. Such implantable devices which provide a controlled dosage of drug to a patient over a long period of time are know in the art. The composition additionally comprises a pharmaceutically acceptable carrier which must not be deleterious to the recipient patient. The carrier must also not have any adverse effect on the active component of the composition, i.e., the human insulin analogue. Suitable carriers and other additives for pharmaceutical compositions which contain therapeutically effective amounts of [10-Aspartic acid-B] human insulin or des-pentapeptide (B26-B30)-[Asp$^{B10}$, Tyr$^{B25}$-α-carboxamide] human insulin or the Glu$^{B10}$ analogue as the active component may be found in U.S. Pat. No. 4,652,547 which provides for insulin-containing compositions.

The invention is further illustrated by the following specific examples which are not intended in any way to limit the scope of the invention. Although specifics are given for the synthesis of [10-aspartic acid-B] human insulin and des-pentapeptide (B26-B30)-[ASP$^{B10}$, Tyr$^{B25}$-α-carboxamide], the same procedures are used to synthesize the Glu$^{B10}$, α-amino-adipic acid$^{B10}$ or other higher B10 homologues.

EXAMPLE 1

Synthesis of [10-Aspartic acid-B] Human Insulin

[10-Aspartic acid-B] human insulin was synthesized by peptide synthesis using fragment condensation techniques. (See, for example, Blake et al., Proc. Natl. Acad. Sci. (1983), vol. 80, pp. 1556–1559 for general techniques.) The homogeneity of all intermediate peptide derivatives was ascertained by thin layer chromatography on 6060 silica gel (Eastman Chromatogram sheet). The solvent systems used to develop the chromatograms were chloroform-methanol-water (45:10:1; 89:10:1; and 200:75:13).

[10-Aspartic acid-B] human insulin was prepared by combinating the S-sulfonated form of human insulin A chain with the synthetic S-sulfonated derivative of human insulin [10-Aspartic acid] B chain in the presence of dithiothreitol as provided in U.S. Pat. No. 4,421,685 to Chance et al. The S-sulfonated human A chain, which is identical with the respective chain of porcine insulin (Nicol et al, Nature (1960), vol. 181, pp. 483–485), was prepared by oxidative sulfitolysis of porcine insulin and separation of the resulting S-sulfonated A and B chains by column chromatography as described by Katsoyannis et al., Biochemistry (1967), vol. 6, pp. 2635–2624. The synthesis of the S-sulfonated human [10-Aspartic acid] B chain was patterned after that of S-Sulfonated natural human B chain as described by Schwartz and Katsoyannis, J. Chem. Soc. Perkin Trans. I (1973), pp. 2894–2901. The C-terminal hexadecapeptide (sequence B$^{15}$–B$^{30}$) was coupled with the adjacent hexapeptide (sequence B$^9$–B$^{14}$) to produce the C-terminal docosapeptide (sequence B$^9$–B$^{30}$). This in turn was coupled with the N-terminal octapeptide (sequence B$^1$–B$^8$) to yield a protected B chain analogue which, upon exposure to liquid hydrogen fluoride and oxidative sulfitolysis of the resulting sulfhydryl derivative, afforded the S-sulfonated form of the [10-Aspartic acid] B chain.

Table I provides some of the compounds and amino acid blocking groups used in the synthesis of the peptides and gives the abbreviations relating thereto.

TABLE I

| Compound | Abbreviation |
|---|---|
| benzyl | Bzl |
| tertiary-butoxycarbonyl | Boc |
| tertiary-butyl | Bu$^t$ |
| cyclohexyl | cHex |
| dicyclohexylamine | DCHA |
| dimethylformamide | DMF |
| dimethylsulfoxide | DMSO |
| diphenylmethyl | DPM |
| N,N'-dicyclohexylcarbodimide | DCC |
| 1-hydroxybenzotriazole | HOBT |
| benzyloxycarbonyl | Z |

A. Synthesis of S-Sulfonated [10-Aspartic acid]B Chains

Z.Glu(cHex).OH,DCHA (Compound I)

This compound was prepared from the respective Boc-derivative (Peninsula Laboratories) by deblocking with trifluoroacetic acid and carbobenzoxylation of the ensuing product. The resulting derivative was crystallized from ether as the dicyclohexylamine salt; mp 131°–132° C. Anal. Calcd for C$_{31}$H$_{48}$N$_2$O$_6$: C,86.4; H. 8.88; N, 5.4. Found: C, 68.3; H, 9.11; N, 5.1.

Z.Glu(cHex)-Ala.OBu$^t$ (Compound II)

Compound I (9.8g) was partitioned between 0.2N H$_2$SO$_4$ and ethyl acetate and the organic layer was separated, washed with water, dried (MgSO$_4$) and concentrated to dryness. To a solution of the residue in DMF (30 ml) cooled to 0° C., H.Ala.OBu$^t$ [prepared from Z.Ala.OBu$^t$ (5.6 g) as described by Schwartz and Katsoyannis, supra] was added followed by HOBT (2.3 g) and DCC (3.7 g). After 24 hr at room temperature, the urea by-product was filtered off and the filtrate was diluted with ethyl acetate (500 ml) and washed successively with 1M NaHCO$_3$, water, 0.2N HCl and water, dried and concentrated, under reduced pressure, to dryness. The product was obtained as an oil [8 g (90%)] which was homogeneous on thin-layer chromatography and was used in the synthesis of the compound III without any further characterization.

Z.Val-Glu(cHex)-Ala.OBu$^t$ (Compound III)

Compound II (8 g) in methanol (150 ml) was hydrogenated over 10% Pd/C catalyst (2 g) for 3 hr. The catalyst was filtered off and the filtrate was concentrated, under reduced pressure, to dryness. The residue was mixed with an activation mixture of Z.Val.OH (4.1 g), HOBT (2.7 g) and DCC (3.3 g) in DMF (30 ml) (activated for 30 min at room temperature before addition of the amino component). After 24 hr the product was isolated in the same manner as described for compound II; oil, 8.7 g (85%). This material was homogeneous on thin-layer chromatography and was used in the following synthetic step without further characterization.

Z.Leu-Val-Glu (cHex)-Ala.OBu$^t$ (Compound IV)

Compound III (8 g) was hydrogenated as described above and the resulting oily residue was dissolved in DMF (30 ml). To this solution Z-leucine p-nitrophenyl ester (5.5 g) and HOBT (1.8 g) were added. After 48 hr, the mixture was diluted with ethyl acetate (250 ml), washed successively with 0.5N NH$_4$OH, water, 0.2N HCl and water, dried (MgSO$_4$) and concentrated to dryness in vacuo. The residue was crystallized from 95% ethanol: wt 8.4 g (88%); mp 190°–194°; [α]D$^{26}$ −20.3° (c 1, DMF). Anal. Calcd for C$_{37}$H$_{58}$N$_4$O$_9$: C, 63.2; H, 8.31; N, 8.0. Found: C, 62.9; H, 8.37; N, 8.1.

Boc.Asp(cHex)-Leu-Val-Glu(cHex)-Ala.OBu$^t$
(Compound V)

Compound IV (1.5 g) was hydrogenated as previously described and the residue was added to an activation mixture of Boc.Asp(cHex). OH (Peninsula Laboratories) (0.8 g), HOBT (0.34 g) and DCC (0.52 g) in DMF (10 ml) (activated for 30 min at room temperature before addition of the amino component). After 24 hr the reaction mixture was processed as described for Compound II, and the product was purified by reprecipitation from ethyl acetate-petroleum ether; wt 1.5 g (85%); mp 203°–205°; [α]D$^{26}$ −8.9° (c 1, DMF). Anal. Calcd for C$_{44}$H$_{75}$N$_5$O$_{12}$: C, 61.0; H, 8.72; N, 8.1. Found: C, 60.7; H, 8.56; N, 7.8.

Boc.Ser(Bzl)-Asp(cHex)-Leu-Val-Glu (cHex)-Ala.OH
(Compound VI)

A solution of compound V (1 g) in trifluoroacetic acid (10 ml) was stored at room temperature for 2 hr and then concentrated to dryness in vacuo and the residue triturated with cold ether. The solid deblocked pentapeptide trifluoracetic acid salt formed was filtered and dried over KOH. An activation mixture of Boc.-Ser(Bzl).OH (1.2 g), HOBT (0.5 g) and DCC (0.6 g) in DMF (10 ml) was prepared and after 30 min incubation, the mixture was filtered into a solution of the pentapeptide trifluoroacetic acid salt in DMSO (10 ml) containing N-methylmorpholine (0.13 ml). After 24 hr the reaction mixture was diluted with cold water (100 ml) and the precipitated product was filtered off, dried and reprecipitated from ethyl acetate-petroleum ether: wt 0.9 g (90%); mp 200°–203°; [α]D$^{26}$ −17.8° (c 1, DMF). Anal. Calcd for C$_{50}$H$_{78}$N$_6$O$_{14}$: C, 60.8; H, 7.96; N, 8.5. Found: C, 61.4; H, 8.25; N, 8.7. Amino acid ratios after acid hydrolysis: Asp$_{1.0}$Ser$_{0.8}$Glu$_{1.0}$Ala$_{1.0}$Val$_{1.1}$Leu$_{1.0}$.

Boc.Ser(Bzl)-Asp(cHex)-Leu-Val-Glu(cHex)-Ala-Leu-Tyr(Bzl)-Leu-Val-Cys(Dpm)-Gly-Glu(Bzl)-Arg(NO$_2$)-Gly-Phe-Phe-Tyr(Bzl)-Thr-Pro-Lys(Z)-Thr(Bzl).OBzl
(Compound VII)

A suspension of the free base of the partially protected hexadecapeptide (sequence B$^{15}$–B+) of human insulin B chain (400 mg) prepared according to Schwartz et al., Int. J. Pept. Protein Res. (1981), vol. 17, pp. 243–255, compound VI (494 mg) and HOBT (80 mg) was stirred until solution occurred. This solution, after the addition of DCC (100 mg), was stirred at 4° C. for 48 hr and then diluted with 95% ethanol (150 ml). The precipitated docosapeptide (sequence B$^9$–B$^{30}$) was filtered off, washed with 95% ethanol and dried: wt 450 mg (88%). Amino acid analysis after acid hydrolysis gave the following composition expressed in molar ratios: Asp$_{1.1}$Thr$_{2.0}$Ser$_{1.0}$Glu$_{2.1}$Pro$_{1.0}$Gly$_{2.2}$Ala$_{0.9}$Val$_{1.9}$Leu$_{2.9}$Tyr$_{1.9}$Phe$_{2.0}$Lys$_{1.1}$Arg$_{0.7}$ (Cys was not determined).

H.Phe-Val-Asn-Gln-His-Leu-Cys(SO$_3$)-Gly-Ser-Asp-Leu-Val-Glu-Ala-Leu-Tyr-Leu-Val-Cys(SO$_3$)-Gly-Glu-Arg-Gly-Phe-Phe-Tyr-Thr-Pro-Lys-Thr.OH
(Human Insulin [10-Aspartic Acid] B Chain S-Sulfonate) (Compound VIII)

A solution of compound VII (400 mg) in a mixture of trifluoroacetic acid-acetic acid (7:3; v/v) (10 ml) was stored at room temperature for 1 hr and then diluted with ether. The precipitated trifluoroacetic acid salt of the docosapeptide was filtered off, washed with ether and dried. A solution of this product in N-methylpyrrolidone (6 ml) and DMF (6 ml) containing triethylamine (0.1 ml) was diluted with ether and dried. This product and Boc.Phe-Val-Asn-Gln-His-Leu-Cys(Dpm)-Gly.OH, prepared according to Schwartz and Katsoyannis, J. Chem. Soc. Perkin Trans. I (1973), pp. 2894–2901, (500 mg) were dissolved in a mixture of DMF (5 ml) and DMSO (5 ml) containing HOBT (90 mg) and then DCC (100 mg) was added. After 48 hr at room temperature, the mixture was poured into cold water (250 ml) containing 1N NH$_4$OH (5 ml) and the precipitated protected triacontapeptide was filtered off, washed (water, 50% methanol and methanol), dried and reprecipitated from DMF-methanol: wt 400 mg (90%).

This product was converted to the S-sulfonated [10-Aspartic acid]B chain by deblocking with liquid hydrogen fluoride followed by oxidative sulfitolysis as described by Schwartz and Katsoyannis, supra, for the synthesis of human insulin B chain S-sulfonate. The protected triacontapeptide (200 mg) was treated with anhydrous liquid hydrogen fluoride (9 ml) containing m-cresol (1 ml) at 0° C. for 1 hr. The hydrogen fluoride was then removed and the residue was triturated successively with ethyl acetate and petroleum ether. To a solution of this product in 8M guanidine hydrochloride (20 ml), buffered with 0.1M Tris-HCl (pH 8.8), sodium sulfite (700 mg) and sodium tetrathionate (500 mg) were added. After 3 hr at room temperature the reaction mixture was placed in dialysis tubing, e.g. Spectrapor ® membrane tubing No. 3, dialyzed against four changes of distilled water (4 l each) at 4° C. for 24 hr, and lyophilized.

For purification the lyophilized material was dissolved in 3 ml of urea acetate buffer (0.04M acetate-8M urea, pH 4.0) and applied to a CM-cellulose column (2.5×40 cm) which was eluted isocratically with the same buffer. See e.g., Katsoyannis et al, Biochemistry (1967), vol. 6 pp. 2635–2642. The column effluent was monitored with a spectrophotometer (ISCO Model U-5A) which gave the elution pattern shown in FIG. 1. The eluate under the main peak (125–168 ml) was collected, dialyzed as described above, and upon lyophilization the S-sulfonated [10-Aspartic acid]B chain was obtained as a white powder: wt 22 mg. Amino acid analysis of the purified chain, after acid hydrolysis gave the following composition expressed in molar ratios, in agreement with the theoretically expected values: Asp$_{2.1}$Thr$_{2.1}$Ser$_{1.1}$Glu$_{3.0}$Gly$_{2.9}$Ala$_{1.0}$Val$_{3.0}$Leu$_{3.8}$Tyr$_{1.8}$Phe$_{2.9}$Lys$_{1.1}$His$_{1.0}$Arg$_{0.9}$ (Cys was not determined).

B. Synthesis and Isolation of [10-Aspartic acid-B] Human Insulin

To a solution of S-sulfonated human (porcine) A chain (40 mg) and S-sulfonated human [10-Aspartic acid-B] chain (20 mg) in 10 ml of 0.1M glycine buffer, pH 10.6, cooled to 4° C., dithiothreitol (7 mg) was added. After 24 hr at 4° C. the mixture was diluted with acetic acid (1 ml) and the resulting precipitate was removed by centrifugation (International Centrifuge, Model HN; 3000 rpm). The supernatant, containing the active material, was passed through a 0.45μ cellulose acetate filter (Sartorius) and subjected to reversed-phase HPLC using a Vydac ® 218 TP column (0.45×25 cm) connected to an LKB liquid chromatography system. Batches (ca 5 mg of protein each) were chromatographed at a flow rate of 0.5 ml/min with a 10 to 50% linear gradient of 2-propanol in 0.1% trifluoroacetic acid over 70 min. The chromatographic pattern is shown in FIG. 2A. Biological assays as described in Examples 2-4 indicated that only the material that eluted at ca 32.3 min had substantial insulin activity. Under these same chromatographic conditions bovine insulin was eluted at 30 min. The fraction containing the active material was concentrated and rechromatographed using the same column and a 20 to 35% linear gradient of 2-propanol in 0.1% trifluoroacetic acid at a flow rate of 0.5 ml/min over 85 min. The elution pattern is shown in FIG. 2B. The fraction containing the active material, eluting at ca 47.2 min, was collected, concentrated and used for the biological studies described in Examples 2-4. Under these same chromatographic conditions bovine insulin was eluted at ca 38 min. From the combination mixture of A and B chains described above, 2 mg of highly purified product was obtained. Amino acid analysis of the purified synthetic material, after acid hydrolysis, gave the following composition, expressed in molar ratios, in good agreement with the theoretically expected values: $Asp_{4.0}Thr_{2.8}Ser_{3.1}Pro_{1.0}Glu_{7.0}Gly_{4.0}Ala_{1.1}Val_{3.4}Ile_{1.4}Leu_{5.9}Tyr_{3.6}Phe_{2.9}Lys_{1.1}His_{1.0}Arg_{1.0}$ (Cys was not determined).

EXAMPLE 2

Analysis of [10-Aspartic acid-B] Human Insulin Potency by Insulin Receptor Binding Assay Receptor binding assays using rat liver plasma membranes were performed as described by Kitagawa et al., Biochemistry (1984), vol. 23, pp. 1405-1413. Rat liver plasma membranes were prepared as described by Horvat et al., Biochem. Biophys. Acta (1975), vol. 382, pp. 609-620.

Briefly, triplicate 0.2-ml incubations contained $^{125}I$-insulin, $3\times10^{-10}M$ unlabeled insulin or [10-Aspartic acid-B] human insulin prepared as in Example 1, and plasma membranes (20-40 μg of protein) in 0.1M sodium phosphate, pH 7.4, containing 0.6% fraction V bovine serum albumin. Following incubation for 45 min at 24° C., the mixtures were diluted with 2.0 ml of ice cold 0.1M sodium phosphate, pH 7.4, containing 0.1% fraction V bovine serum albumin and immediately filtered through cellulose-acetate filters. The filters were washed twice with the ice cold buffer, dried, and then radioactivity was counted in a scintillation counter using Filtron-X ®. Nonspecific binding, defined as radioactivity remaining on the filters when the incubations contained $1\times10^{-5}M$ unlabeled insulin, was subtracted from all values. Relative potency was obtained as the concentration ratio of unlabeled insulin to [10-Aspartic acid-B] human insulin required to inhibit 50% of the specific binding of $^{125}I$-insulin to the receptor preparation.

Figure 3:
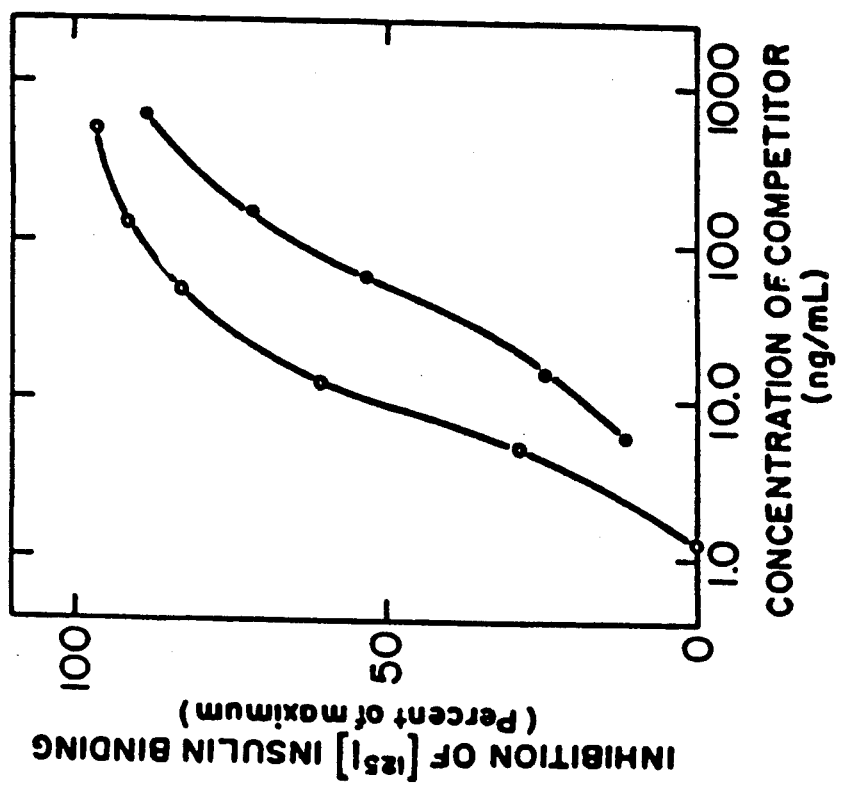
FIG. 3 is a graph showing the competitive inhibition of $^{125}$I-insulin binding to rat liver plasma insulin receptors by [10-Aspartic acid-B] human insulin ( ) and bovine insulin ( ).

FIG. 3 depicts the ability of bovine insulin ( ) and [10-Aspartic acid-B] human insulin (o) to compete with $^{125}I$-insulin in binding to insulin receptors in rat liver plasma membranes. Inhibition of binding, expressed as per cent of maximum, was plotted as a function of competitor concentration. The data points shown in FIG. 3 represent the mean of triplicate determinations in a representative assay which was performed four times. The maximum binding in these assays amounted to 8.2% of the input radioactivity.

As can be seen from FIG. 3, the dose response curves of [10-Aspartic acid-B] human insulin and bovine insulin were essentially parallel. The potency of [10-Aspartic acid-B] human insulin calculated as provided above, however, was about 534±146% relative to bovine insulin.

EXAMPLE 3

Analysis of [10-Aspartic acid-B] Human Insulin Potency by Lipogenesis Assays

Lipogenesis assays to measure the potency of the insulin analogue were performed as described by Kitagawa et al., supra. The assays measured the ability of the insulin analogue as compared to bovine insulin to convert, [3-$^3$H] glucose into lipids.

Adipocytes were prepared by incubating epididymal and perirenal fat pads obtained from male rats weighing 200-300 g with 1.0 mg/ml collagenase for 60 min at 37° C., followed by filtration through gauze and then through fine-mesh silk. Cells were washed twice by flotation in a clinical centrifuge before suspension for use. The incubation medium was Krebs-Ringer bicarbonate containing half the recommended calcium, 0.5 mM glucose, and 3% fatty acid free bovine serum albumin, with 95% $O_2$-5% $CO_2$ as the gas phase. Triplicate lipogenesis incubations contained 1.0 ml of adipocyte suspension (20-40 mg dry wt cells) and bovine insulin or [10-Aspartic acid-B] human insulin, prepared as in Example 1. Cells were preincubated for 45 min at 37° C. before the addition of [3-$^3$H] glucose. Incubation was continued for 60 min and stopped by the addition of 0.2 ml of 5N $H_2SO_4$ and 0.2 ml of corn oil to aid in the extraction of lipids. Samples were extracted with 10 ml of Soluscint-0 ® for 30 min at room temperature before counting the radioactivity in a scintillation counter. Under these conditions, [3-$^3$H] glucose was not extracted into the organic phase containing the scintillation fluors and was essentially uncounted. Zero and 100% stimulation of lipogenesis were defined as radioactivity observed in the absence and presence, respectively, of $9.1\times10^{-10}M$ insulin (5.5 ng/ml). Relative potency was obtained as the concentration ratio of insulin to [10-Aspartic acid-B] human insulin required to produce 50% of the maximum stimulation of lipogenesis.

FIG. 4 shows the stimulation of the conversion of [3-$^3$H] glucose into organic-extractable material (i.e., lipids) in isolated rat adipocytes by [10-Aspartic acid-B] human insulin ( ) prepared as in Example 1 and bovine insulin ( ). Stimulation, expressed as per cent of maximum, was plotted as a function of the agonist concentration. The data points represent the mean of triplicate determinations in representative assays performed four times. In the assays, 0% and 100% stimulation refer to 0.3 and 3.5 nmol glucose per mg cells per hr, respectively.

The data represented in FIG. 4 shows that [10-Aspartic acid-B] human insulin was a full agonist in the assays, reaching the same maximum stimulation of lipogenesis as the natural bovine insulin. The relative potency of [10-Aspartic acid-B] human insulin, however, was calculated to be 435±144% relative to the bovine insulin.

The potency values calculated for [10-Aspartic acid-B] human insulin in the receptor binding assays of Example 2 and the present lipogenesis assays were determined to be not statistically different (0.4>p>0.3 by Student's t-test).

It is, thus, readily apparent that [10-Aspartic acid-B] human insulin, is a superactive insulin displaying in vitro potency about five times greater than natural insulin.

EXAMPLE 4

Radioimmunoassay Analysis of [10-Aspartic acid-B] Human Insulin

Radioimmunoassay analyses as described by Kitagawa et al., supra, were carried out to assess whether [10-Asparticacid-B] human insulin was immunologically distinguishable from natural insulin.

Guinea pig antiserum to porcine insulin and goat anti-guinea pig-γ globulin were used at a 1:25 dilution in assay buffer (sodium phosphate, 0.04M, pH 7.6, containing 0.154M NaCl, 0.1% gelatin, and 0.01% thimerosal). Duplicate assay tubes contained 0.1 ml of anti-insulin antiserum, 0.072 ng of $^{125}$I-insulin, and bovine insulin (0.06-0.36 ng) or [10-Aspartic acid-B] human insulin prepared as in Example 1 (1-4.0 ng) in a total volume of 0.8 ml. After incubation at room temperature overnight, 0.2 ml of the precipitating antibody (goat anti-guinea pig-γ globulin) was added, and the tubes were further incubated overnight at room temperature. Immune precipitates were collected on cellulose-acetate filters and washed with two successive 1.0 mL portions of ice-cold assay buffer. Filters were dried and radioactivity was counted in a scintillation counter in Filtron-X ®. Straight-line plots of $C_o/C_i$ were constructed by linear regression analysis as described by Hales et al., Biochem. J. (1963), vol. 88, pp. 137-146, and the potency of [10-Aspartic acid-B] human insulin relative to bovine insulin was obtained as the ratio of the slopes of such plots.

Synthetic [10-Aspartic acid-B] human insulin exhibited approximately equal potency to bovine or porcine insulin in the radioimmunoassays. This result indicated that the substitution of aspartic acid for histidine at position $B^{10}$ did not have a significant effect on the immunogenic determinants of the molecule.

EXAMPLE 5

Synthesis of Des-pentapeptide (B26-B30)-[Asp$^{B10}$, Tyr$^{B25}$-α-carboxamide] Human Insulin Des-pentapeptide (B26-B30)-[Asp$^{B10}$, Tyr$^{B25}$-α-carboxamide] human insulin was synthesized by peptide synthesis using fragment condensation techniques. (See, for example, Blake et al., Proc. Natl. Acad. Sci. (1983), vol. 80, pp. 1556-1559 for general techniques.) The homogeneity of all intermediate peptide derivatives was ascertained by thin layer chromatography on 6060 silica gel (Eastman Chromatogram sheet). The solvent systems used to develop the chromatograms were chloroform-methanol-water (45:10:1; 89:10:1; and 200:75:13).

Des-pentapeptide (B26-B30)-[Asp$^{B10}$, Tyr$^{B25}$-α-carboxamide] human insulin was prepared by combining the S-sulfonated form of human insulin A chain with the synthetic S-sulfonated derivative of human insulin des-pentapeptide (B26-B30)-[Asp10, Tyr-α-carboxamide25] B chain in the presence of dithiothreitol as provided in U.S. Pat. No. 4,421,685 to Chance et al. The S-sulfonated human A chain, which is identical with the respective chain of porcine insulin (Nicol et al, Nature (1960), vol. 181, pp. 483-485), was prepared by oxidative sulfitolysis of porcine insulin and separation of the resulting S-sulfonated A and B chains by column chromatography as described by Katsoyannis et al., Biochemistry (1967), vol. 6, pp. 2635-2624. The synthesis of the S-sulfonated doubly modified B chain was assembled by stepwise solid-phase synthesis using 4-methylbenzhydrylamine resin as the solid support (0.5 mmol of amine per g; 1 g), as described by Merrifield, J. Am. Chem. Soc., 85:2149-54 (1963) and Barany et al., "The Peptides", Gross et al., eds., 2:1-284, Academic Press (New York, 1980). The Boc group was used for N$^α$ protection except for the N-terminal phenylalanine residue which was protected by the benzyloxycarbonyl group.

Table II provides some of the compounds and amino acid blocking groups used in the synthesis of the peptides.

TABLE II

| Compound | Protected |
|---|---|
| benzyl | serine |
| cyclohexyl | glutamic and aspartic acids |
| benzyloxymethyl | histidine |
| 2,6-dichlorobenzyl | tyrosine |
| N$^G$-p-toluenesulfonyl | arginine |
| 4-methylbenzyl | cysteine |

A manual double coupling protocol was followed, in accordance with Merrifield et al., Biochem., 21:5020-31 (1982), using activated protected amino acids (1-hydroxybenzotriazole-di-cyclohexylcarbodiimide, in dimethyformamide) in three-fold excess. The completion of the reaction was monitored by the qualitative ninhydrin test of Kaiser et al., Anal. Biochem., 34:595-98 (1970) and was negative after each double coupling.

After the chain was assembled the peptide-resin was washed extensively with methylene chloride and methanol and then dried to a final weight of 3.0 g. A portion of this product (700 mg) was deprotected by the low-high hydrogen fluoride procedure according to Tam et al., J. Am Chem. Soc., 105:6442-55 (1983). In the first step the peptide-resin was treated with a mixture consisting of p-cresol (1 ml), dimethylsulfide (6.5 ml) and liquid hydrogen fluoride (2.5 ml). After 2 hours at 0° C. the mixture was concentrated under vacuum and the residue was treated with liquid hydrogen fluoride (10 ml) for 1 hour at 0° C. The hydrogen fluoride was then removed and the residue was triturated with ethyl acetate and petroleum ether. Sodium sulfite (700 mg) and sodium tetrathionate (500 mg) were added to a suspension of this product in 8M guanidine hydrochloride (20 ml) buffered with 0.1M Tris.HCl (pH 8.8). After 3 hours at room temperature the reaction mixture was filtered to remove the resin, and the filtrate was placed in Spectrapor membrane tubing no. 3, and dialyzed against four changes of distilled water (4 liters each) at 4° C. for 24 hours. Lyophilization of the dialyzate afforded the crude S-sulfonated B chain analogue as a white powder weighing 250 mg.

Figure 5:
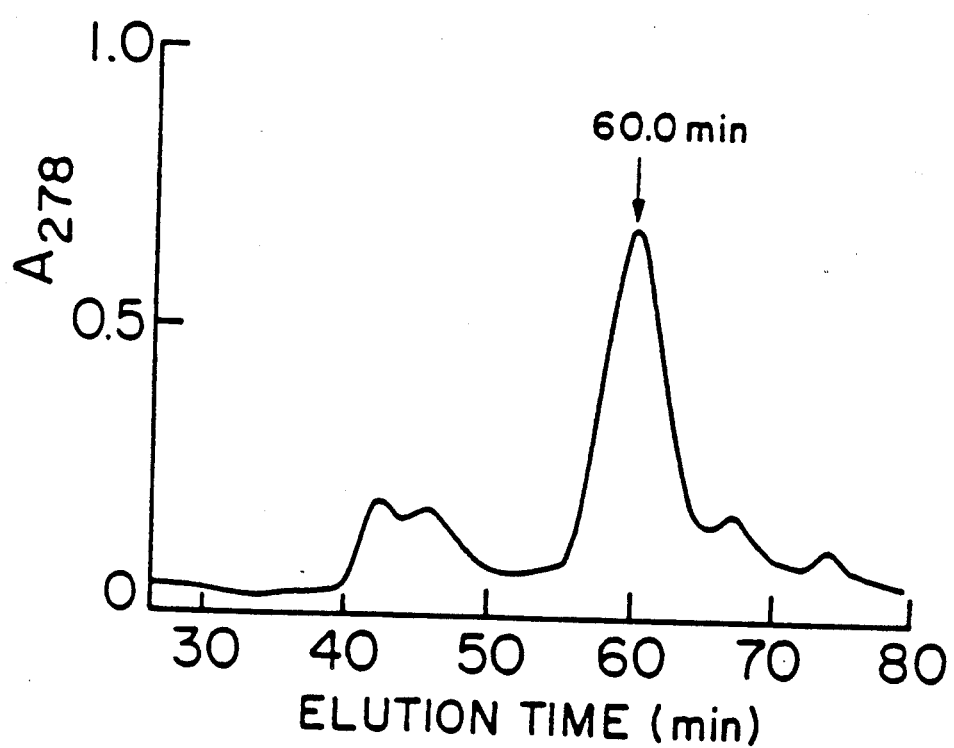
FIG. 5 is a chromatogram showing the elution of crude human des-pentapeptide (B26-B30)-[Asp10, Tyr-α-carboxamide25] B chain S-sulfonate from a CM-cellulose column.

The lyophilized material was dissolved in a mixture of water:2-propanol (2:1, v/v) containing 0.02M Tris.HCl, pH 7.5 and purified by high-performance liquid ion-exchange chromatography on a Synchropak AX 300 column (1×25 cm) connected to an LKB liquid chromatography system. Batches of about 70 mg of protein each were chromatographed at a flow rate of 1.5 ml/min with a 0–80% linear gradient of 0.5M sodium chloride in the above-mentioned solvent, over 140 minutes. The chromatographic pattern is shown in FIG. 5. The effluent under the main peak (around 60 min) was concentrated under vacuum to approximately 50% of its original volume, dialyzed against distilled water (Spectrapor membrane tubing no. 3) and lyophilized. From the 250 mg of crude material 150 mg of purified product was obtained as a white fluffy powder. Amino acid analysis of the purified S-sulfonated B chain analogue after acid hydrolysis gave the following composition, expressed in molar ratios, in agreement with the theoretically expected values (shown in parenthesis): $Asp_{1.9(2)}Ser_{1.0(1)}Glu_{3.0(3)}Gly_{3.0(3)}Ala_{1.1}$ (1) $Val_{2.7(3)}Leu_{3.8(4)}Tyr_{1.9(2)}Phe_{2.0(2)}His_{0.9(1)}Arg_{1.0(1)}$ (Cysteine was not determined).

EXAMPLE 6

Figure 6A:
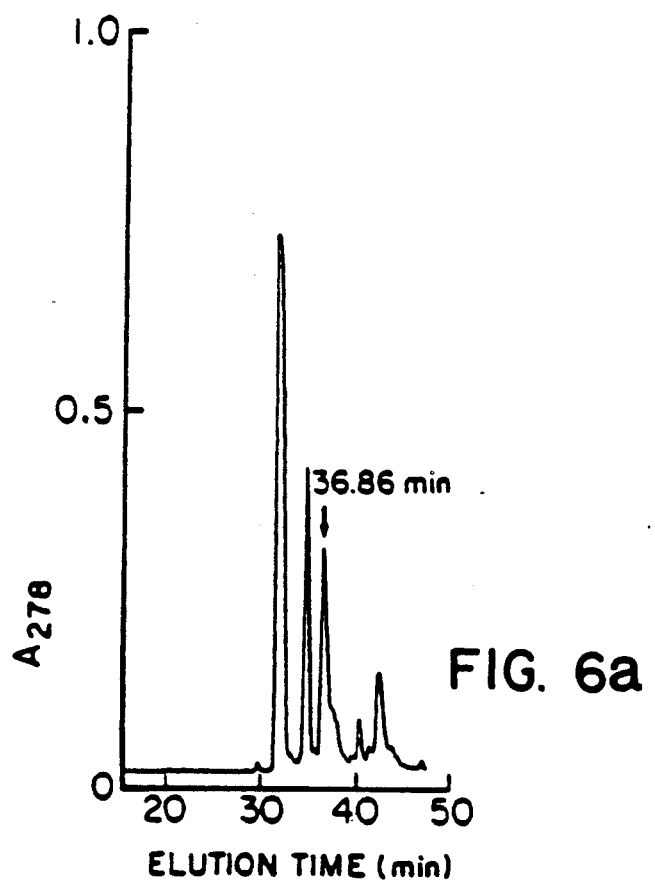
FIG. 6 is an HPLC chromatogram showing the elution of the combination mixture of human A chain S-sulfonate and human des-pentapeptide (B26-B30)- [Asp10, Tyr-α-carboxamide25] B chain S-sulfonate. Panel A shows the initial chromatographic separation. Panel B depicts the rechromatography of the material in the peak eluting at 36.86 min shown in Panel A.
Figure 6B:
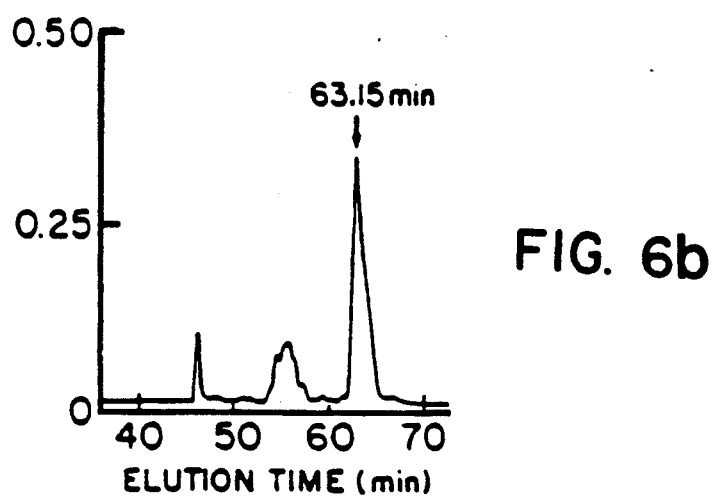

Synthesis and Isolation of Des-pentapeptide (B26-B30)-[$Asp^{B10}$, $Tyr^{B25}$-α-carboxamide] Human Insulin Dithiothreitol (3.5 mg) was added to a solution of S-sulfonated human (porcine) A chain (20 mg) and S-sulfonated human des-pentapeptide (B26-B30)-[Asp10, Tyr-α-carboxamide25] B chain (10 mg) in 6 ml of 0.1M glycine buffer, pH 10.6, cooled to 4° C. After 24 hours at 4° C. the mixture was diluted with glacial acetic acid (1 ml) and the resulting precipitate was removed by centrifugation (International Centrifuge, Model HN; 3000 rpm). The supernatant, containing the active material, was passed through a 0.45μ cellulose acetate filter (Sartorius) and subjected to reversed-phase HPLC using a Vydac® 218 TP column (0.45×25 cm) connected to an LKB liquid chromatography system. Batches of about 5 mg of protein each were chromatographed at a flow rate of 0.5 ml/min with a 10 to 50% linear gradient of 2-propanol in 0.1% trifluoroacetic acid over 70 min. The chromatographic pattern is shown in FIG. 6A. The fraction containing the active material, as determined by insulin assays, was concentrated and rechromatographed using the same column and a 20 to 35% linear gradient of 2-propanol in 0.1% trifluoroacetic acid at a flow rate of 0.5 ml/min over 110 min. The elution pattern is shown in FIG. 6B. The fraction containing the active material, eluting at approximately 63.1 min, was collected and lyophilized. From the mixture of A and B chains described above, 1.4 mg of highly purified product was obtained. Amino acid analysis of the purified synthetic material, after acid hydrolysis, gave the following composition, expressed in molar ratios, in good agreement with the theoretically expected values:

$Ala_{4.1(4)}Thr_{0.9(1)}Ser_{3.0(3)}Glu_{7.0(7)}Gly_{3.8(4)}Ala_{1.1(1)}Val_{3.3(4)}Ile_{1.4(2)}Leu_{6.0(6)}Tyr_{3.8(4)}Phe_{2.0(2)}His_{1.0(1)}Arg_{0.9(1)}$ (Cysteine was not determined).

EXAMPLE 7

Analysis of Des-pentapeptide (B26-B30)-[$Asp^{B10}$, $Tyr^{B25}$-α-carboxamide] Human Insulin Potency by Insulin Receptor Binding Assay The same assay was used as in Example 2.

Figure 7:
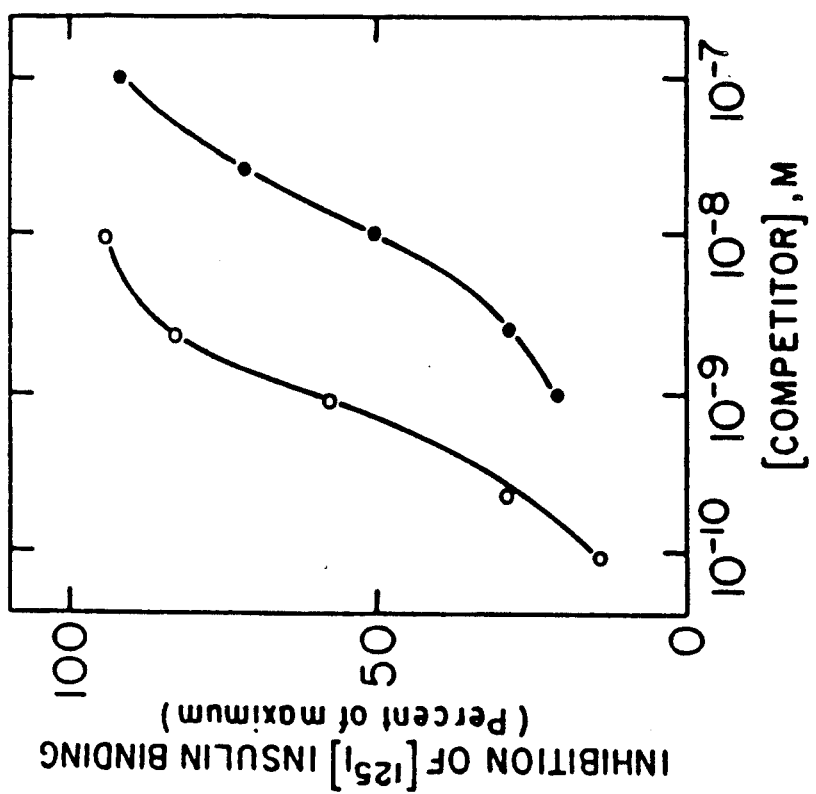
FIG. 7 is a graph showing the competitive inhibition of $^{125}$I-insulin binding to rat liver plasma insulin receptors by des-pentapeptide (B26-B30)-[Asp$^{B10}$, Tyr$^{B25}$-α-carboxamide] human insulin ( ) and bovine insulin ( ).

FIG. 7 depicts the ability of bovine insulin ( ) and des-pentapeptide (B26-B30)-[$Asp^{B10}$, $Tyr^{B25}$-α-carboxamide] human insulin (o) to compete with $^{125}$I-insulin in binding to insulin receptors in rat liver plasma membranes. Inhibition of binding, expressed as per cent of maximum, was plotted as a function of competitor concentration. The data points shown in FIG. 7 represent the mean of triplicate determinations in a representative assay which was performed four times using three different preparations of the synthetic compound. In these assays, binding of $^{125}$I-insulin in the absence of competitor amounted to 9.1% of the input radioactivity, and non-specific binding amounted to 9.6% of total binding.

As can be seen from FIG. 7, the synthetic compound displaced 50% of specifically bound $^{125}$insulin at a concentration more than ten-fold lower than the concentration required for natural insulin. The potency of despentapeptide (B26-B30)-[$Asp^{B10}$, $Tyr^{B25}$-α-carboxamide] human insulin calculated as provided above, however, was about 1166±31.2% relative to bovine insulin.

EXAMPLE 8

Analysis of Des-pentapeptide (B26-B30)-[$Asp^{B10}$, $Tyr^{B25}$-α-carboxamide] Human Insulin Potency by Lipogenesis Assays The same assay was used as in Example 3.

Figure 8:
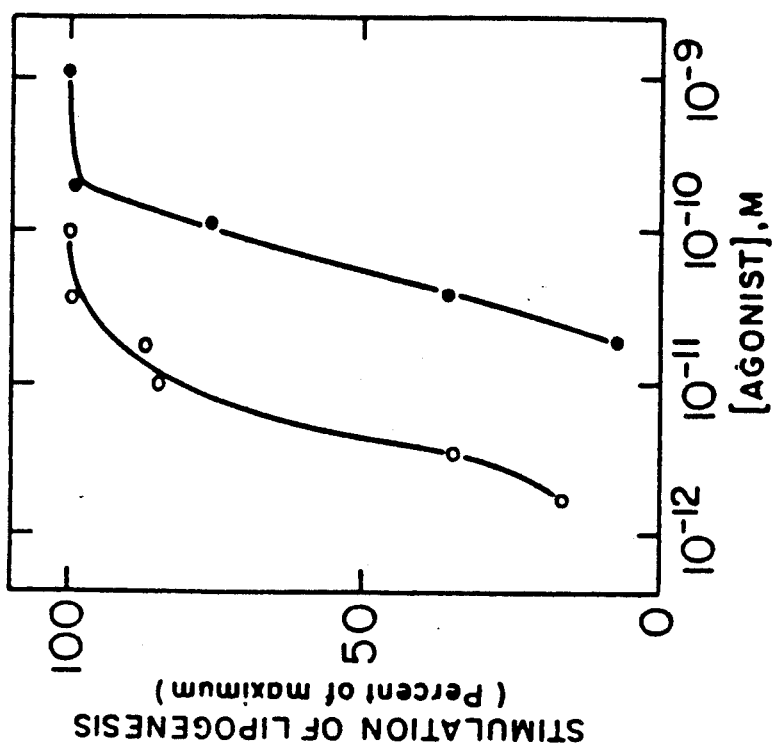
FIG. 8 is a graph showing the effect of des-pentapeptide (B26-B30)-[Asp$^{B10}$, Tyr$^{B25}$-α-carboxamide] human insulin and bovine insulin on the stimulation of lipogenesis in rat adipocytes.

FIG. 8 shows the stimulation of [3-$^3$H] glucose into organic-extractable material (i.e., lipids) in isolated rat adipocytes by des-pentapeptide (B26-B30)-[$Asp^{B10}$, $Tyr^{B25}$-α-carboxamide] human insulin ( ) prepared as in Example 5 and bovine insulin ( ). Stimulation, expressed as per cent of maximum, was plotted as a function of the agonist concentration. The data points represent the mean of triplicate determinations in representative assays performed four times using three different preparations of the synthetic compound. In the assays, 0% and 100% stimulation refer to 11.4 and 78.8 nmol glucose per mg cells per hr, respectively.

The data represented in FIG. 8 shows that des-pentapeptide (B26-B30)-[$Asp^{B10}$, $Tyr^{B25}$-α-carboxamide] human insulin produced half-maximal stimulation of lipogenesis at a much lower concentration than that required for natural bovine insulin. The relative potency of des-pentapeptide (B26-B30)-[[$Asp^{B10}$, $Tyr^{B25}$-α-carboxamide] human insulin was calculated to be 1352±114% relative to the bovine insulin. The maximum stimulation of lipogenesis was the same for both compounds.

It is, thus, readily apparent that des-pentapeptide (B26-B30)-[$Asp^{B10}$, $Tyr^{B25}$-α-carboxamide] human insulin, is a superactive insulin displaying in vitro potency eleven to thirteen times greater than natural insulin.

The isolated des-pentapeptide (B26-B30)-[$Glu^{B10}$, $Tyr^{B25}$-α-carboxamide] human insulin prepared by an identical procedure as the $Asp^{B10}$ analogue displayed a potency about twenty times greater than natural insulin.

EXAMPLE 9

Radioimmunoassay Analysis of Des-pentapeptide (B26-B30)-[$Asp^{B10}$, $Tyr^{B25}$-α-carboxamide] Human Insulin The same assay was used as in Example 4.

Synthetic des-pentapeptide (B26-B30)-[$Asp^{B10}$, $Tyr^{B25}$-α-carboxamide] human insulin exhibited approximately equal potency to bovine insulin in the radioimmunoassays. This result indicated that the structural differences that give rise to stronger binding to the insulin receptor and the concomitantly higher in vitro insulin-like activity displayed by the synthetic compound did not have a significant effect on the immunogenic determinants of the molecule.

DISCUSSION OF THE EXAMPLES

Prior X-Ray analyses have indicated that histidine at position $B^{10}$ resides at the surface of the insulin monomer and is important in the formation of zinc insulin hexamers. See, e.g. Blondell et al., Adv. Prot. Chem. (1972), vol. 26, pp. 279–402. Previous studies have shown that replacement of histidine at position $B^{10}$ with leucine, lysine, or asparagine produced synthetic insulin analogues displaying reduced biological potency, ca 14 to 45%, relative to the natural hormone. See, Schwartz et al., J. Chem. Res. (S), pp. 220–221, J. Chem. Res. (M), pp. 2453–2469 (1977); Schwartz et al., J. Prot. Chem. (1982), vol. 1, pp. 177–189; Burke et al., Int. J. Protein Res. (1984), vol. 23, pp. 394–401. From these studies it had been concluded that hydrophilicity at $B^{10}$ per se was relatively unimportant in determining biological activity of insulin and the presence of a strongly basic amino acid residue at that position was deleterious. It had been further suggested that the ability to exist in either a protonated or unprotonated state near physiological pH, a property unique to a histidine residue, was believed to be a requirement at position for high biological activity. See, e.g., Burke et al., supra. [10-Aspartic acid-B] human insulin, which at physiological pH would have a negative charge at the $B^{10}$ position, however, was found to be several fold more active than natural insulin in in vitro experiments as shown in the Examples.

The superactivity of [10-Aspartic acid-B] human insulin apparently results from stronger binding to the insulin receptor. It is believed that the stronger binding of the analogue to the receptor may be due to a change in conformation of the analogue more favorable for binding to the receptor, resulting from intramolecular interactions involving the negative charge at position $B^{10}$ (e.g., a salt bridge). Alternatively, the stronger binding may result from a direct interaction with a complementary surface on the receptor containing a positive charge. In reversed-phase HPLC, as shown in FIG. 2, [10-Aspartic acid-B] human insulin, under two chromatographic conditions, eluted significantly later than natural insulin. This behavior indicated that the synthetic analogue was a more apolar molecule. The large difference in polarity exhibited between natural insulin and [10-Aspartic acid-B] human insulin cannot be ascribed to the substitution of one hydrophilic residue for another. It is believed that the most reasonable explanation for the difference in polarity is that it reflects a change in conformation which is believed to result in stronger binding of the analogue to the insulin receptor.

Des-pentapeptide (B26-B30)-[$Asp^{B10}$, $Tyr^{B25}$-α-carboxamide] human insulin incorporates, two modifications which, when individually introduced into the insulin molecule, lead to analogues displaying higher potency than the natural hormone. These individual modifications are (i) elimination of the B26-B30 segment and substitution of Phe B25 with Tyr-α-carboxamide, and (ii) replacement of His B10 with Asp. This analogue, des-pentapeptide(B26-B30)-[$Asp^{B10}$, -$Tyr^{B25}$-α-carboxamide] human insulin, is the most potent insulin analogue yet described. Its biological activity is greater than the sum of the enhanced potencies displayed by analogues containing either modification alone. This finding suggests that the B25 and B10 sites may modulate the conformation of distinct receptor-binding regions of insulin to high receptor binding affinity states. In fact, the high association constant of the insulin-receptor complex in various tissues (approximately $10^9 M^{-1}$) would appear to require the concerted action of several binding species. The histidine residue at position B10 is not one of the residues proposed to contribute to the recognition of insulin by its receptor. Blundell et al., Adv. Protein Chem., 26:279–482 (1972); Blundell et al., Nature (London), 257:197–203 (1975); Pullen et al., Nature (London), 259:369–72 (1976). However, the increased potency of [$Asp^{B10}$] insulin ([10-Aspartic acid-B] insulin), as well as the reduced potency of [$Leu^{B10}$]-, [$Asn^{B10}$]-, and [$Lys^{B10}$] insulins described in Schwartz et al., J. Chem. Res., 220–21 (1977); Schwartz et al., J. Protein Chem., 1:177–89 (1982); and Burke et al., Int. J. Pept. Prot. Res., 23:394–401 (1984), demonstrate that substitutions at this position can have profound effects upon the ability of the resulting molecules to interact with the insulin receptor and initiate a biological response. Whether the B10 site is an element of a receptor-binding region, or whether the modifications at that site affect a distal binding region cannot be unambiguously determined from the available data. Many models can be proposed to account for the very high potencies of the present analogues. The B25 and B10 sites could be elements of distinct receptor-binding regions of insulin which may be individually modulated by the modifications at the B25 and B10 positions respectively leading, in the present analogues, to high-affinity states for receptor binding. In addition the B25 and B10 modifications may independently and in concert favorably affect the conformation of other distinct regions which constitute important receptor binding domains of insulin.

We claim:

1. A method of treating diabetes in a patient in need of such treatment comprising administering to the patient a therapeutically effective amount of a superactive insulin analogue selected from the group consisting of des-pentapeptide (B26-B30)-[ $Asp^{B10}$, $Tyr^{B25}$-α-carboxamide] human insulin and des-pentapeptide (B26-B30)-[$Glu^{B10}$, $Tyr^{B25}$-α-carboxamide] human insulin together with a pharmaceutically acceptable carrier.

2. Method according to claim 1 in which the superactive insulin analogue is administered intramuscularly.

3. Method according to claim 1 in which the superactive insulin analogue is administered subcutaneously.

4. Method according to claim 1 in which the superactive insulin analogue is administered intravenously.

5. Method according to claim 1 in which the superactive insulin analogue is administered by an implantable pump.

6. A superactive insulin analogue having the formula

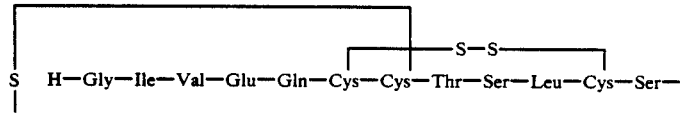

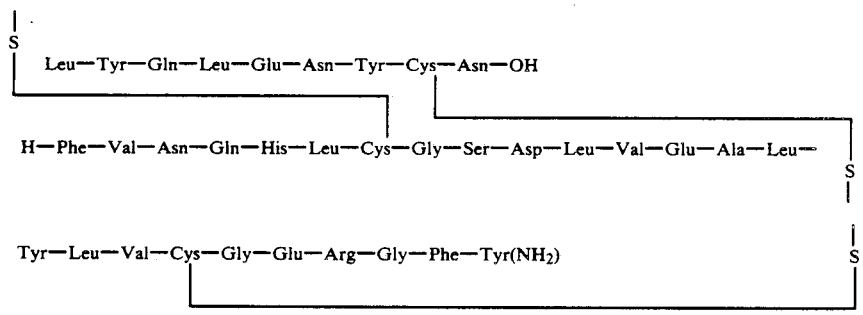

7. A superactive insulin analogue having the formula

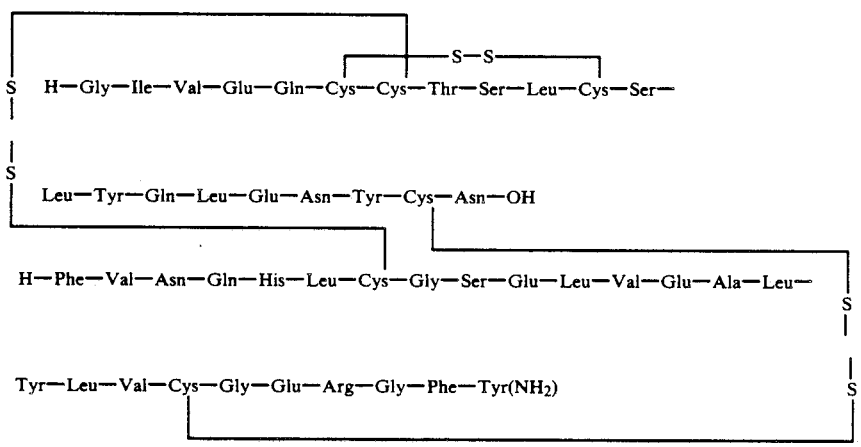

8. A superactive insulin analogue having the formula

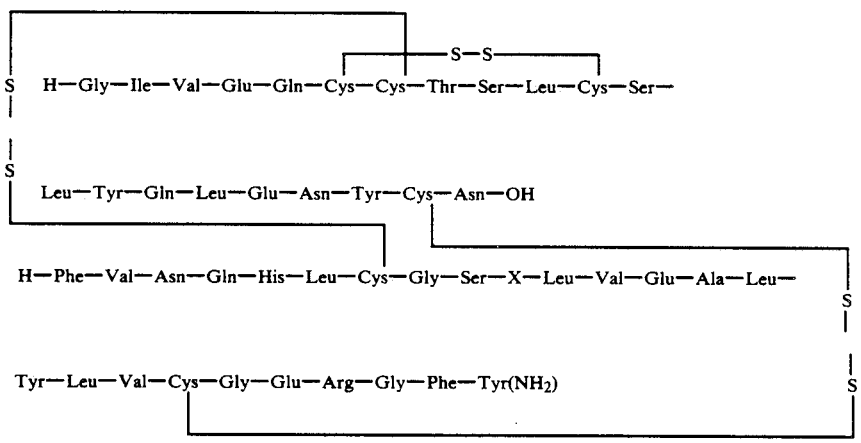

wherein x is an α-amino-adipic acid or a homologue thereof.

9. A pharmaceutical composition for the treatment of diabetes in a patient in need of such treatment comprising a therapeutically effective amount of a superactive human insulin analogue selected from the group consisting of des-pentapeptide (B26-B30)-[Asp$^{B10}$, Tyr$^{B25}$-α-carboxamide] human insulin and des-pentapeptide (B26-B30)-[Glu$^{B10}$, Tyr$^{B25}$-α-carboxamide] human insulin together with a pharmaceutically acceptable carrier.

* * * * *

UNITED STATES PATENT AND TRADEMARK OFFICE
CERTIFICATE OF CORRECTION

Page 1 of 3

PATENT NO. : 4,992,417
DATED : February 12, 1991
INVENTOR(S) : Katsoyannis et al.

It is certified that error appears in the above-identified patent and that said Letters Patent is hereby corrected as shown below:

Column 14, line 59, after "$Ser_{1.1}$" insert --$Pro_{1.1}$--.

Column 15, line 64, delete "( )" and substitute --(o)-- therefor.

Column 16, lines 55 and 56, delete "( )" and substitute --(o)-- therefor.

Column 19, line 53, delete "$Ala_{4.1(4)}$" and substitute --$Asp_{4.1(4)}$-- therefor.

Column 19, line 62, delete "( )" and substitute --(o)-- therefor.

Column 20, line 25, delete "( )" and substitute --(o)-- therefor.

Column 20, line 26 delete "( )" and substitute --(o)-- therefor.

Column 21, line 23, after the word "position" insert --$B^{10}$--.

UNITED STATES PATENT AND TRADEMARK OFFICE
CERTIFICATE OF CORRECTION

Page 2 of 3

PATENT NO. : 4,992,417

DATED : February 12, 1991

INVENTOR(S) : Katsoyannis et al.

It is certified that error appears in the above-identified patent and that said Letters Patent is hereby corrected as shown below:

Page 2 of References Cited, second column, between lines 20 and 21 insert --Ferderigos, N., Burke, G.T., Kitawaga, K., and Katsoyannis, P.G.,--

Page 2 of References Cited, second column, seventh-from-bottom line, delete "Glycin" and substitute --Glycine-- therefor.

Column 1, line 5, after the words "filed July 17, 1987." insert --This invention was made with government support under grant #DK-12925 awarded by the National Institutes of Health. The government has certain rights in the invention.--

Column 6, lines 27 and 28, delete "( )" and substitute --(o)-- therefor.

UNITED STATES PATENT AND TRADEMARK OFFICE
CERTIFICATE OF CORRECTION

PATENT NO. : 4,992,417

DATED : February 12, 1991

INVENTOR(S) : Katsoyannis et al

It is certified that error appears in the above-identified patent and that said Letters Patent is hereby corrected as shown below:

Column 6, lines 46 and 47, delete "( )" and substitute --(o)-- therefor.

Column 11, line 11, delete "know" and substitute --known-- therefor.

Column 12, line 16, delete "dicyclohexlycarbodimide" and substitute --dicyclohexylcarbodimide-- therefor.

Column 13, line 54, delete "$B^{15}-B^+$" and substitute --$B^{15}-B^{30}$-- therefor.

Signed and Sealed this

Twenty-ninth Day of September, 1992

Attest:

DOUGLAS B. COMER

Attesting Officer

Acting Commissioner of Patents and Trademarks